(12) United States Patent
Luthra et al.

(10) Patent No.: US 8,221,720 B2
(45) Date of Patent: Jul. 17, 2012

(54) PURIFICATION METHODS

(75) Inventors: Sajinder Kaur Luthra, London (GB); Frank Brady, London (GB); Nicholas Toby Jeffery, Caerphilly (GB); Erik Arstad, London (GB); Alexander Mark Gibson, Amersham (GB); Duncan Wynn, Amersham (GB); Alan Cuthbertson, Oslo (NO); Magne Solbakken, Oslo (NO)

(73) Assignees: Hammersmith Imanet Limited, London (GB); GE Healthcare Limited, Buckinghamshire (GB); GE Healthcare AS, Oslo (NO)

( * ) Notice: Subject to any disclaimer, the term of this patent is extended or adjusted under 35 U.S.C. 154(b) by 973 days.

(21) Appl. No.: 10/560,508

(22) PCT Filed: May 11, 2005

(86) PCT No.: PCT/GB2005/001796
§ 371 (c)(1),
(2), (4) Date: Jan. 29, 2007

(87) PCT Pub. No.: WO2005/107819
PCT Pub. Date: Nov. 17, 2005

(65) Prior Publication Data
US 2007/0148647 A1    Jun. 28, 2007

(30) Foreign Application Priority Data
May 11, 2004 (GB) .................................. 0410448.5

(51) Int. Cl.
*A61K 51/00* (2006.01)
*A61M 36/14* (2006.01)
(52) U.S. Cl. ............... 424/1.89; 424/1.11; 424/1.65; 424/1.81; 424/1.85
(58) Field of Classification Search .............. 424/1.11, 424/1.49, 1.57, 1.65, 1.69, 1.73, 1.81, 1.85, 424/1.89, 9.1, 9.3, 9.4, 9.5, 9.6, 9.7, 9.8, 424/400
See application file for complete search history.

(56) References Cited

U.S. PATENT DOCUMENTS

| 5,290,925 A * | 3/1994 | Fino ........................... 536/25.32 |
| 5,622,826 A | 4/1997 | Varma et al. |
| 7,115,249 B2 * | 10/2006 | Luthra et al. ................. 424/1.89 |
| 7,223,891 B2 * | 5/2007 | Brady et al. ................... 570/101 |
| 7,405,332 B2 * | 7/2008 | Brady et al. ................... 570/162 |
| 2003/0143570 A1 | 7/2003 | Abrams et al. |

FOREIGN PATENT DOCUMENTS

| WO | 97/42230 | 11/1997 |
| WO | 99/18053 | 4/1999 |
| WO | 0119484 | 3/2001 |
| WO | 01/98378 | 12/2001 |

OTHER PUBLICATIONS

PCT/2005/001796 Int'l Search Report dated Aug. 2005.
GB 0410448.5 Search Report dated Oct. 2004.
Booth, et.al., "Polymer-Supported Quenching Reagents for Parallel Purification" J. Am. Chem.. Soc., 1997, 199, pp. 4882-4886.
Eames, et.al., "Polymeric Scavenger Reagents in Organic Synthesis" Eur. J. Org. Chem. 2001, pp. 1213-1224.
Kaldor, et.al., "Use of Solid Supported Nucleophiles and Electrophiles for the Purification of Non-Peptide Small Molecule Libraries" Tetrahedron Letters, vol. 37, No. 40. pp. 7193-7196.
Stabile-Harris, et.al., "Automated Purification Systems" Laboratory Automation in the Chemical Industries, (2002) pp. 111-132.
Weinbrenner, "Purification Principles in High-Speed Solution-Phase Synthesis" Methods & Principles in Medicinal Chemistry, (2000) 9 (Combinatorial Chemistry) 22-46.
Osman, S. et.al. Comparative biostribution and metabolism of carbon-11-labeled N-[2-(dimethylamino)ethyl] acridine-4-carboxamide and DNA-intercalating analogues, Cancer Research 2001, vol. 61, No. 7, pp. 2935-2944.

* cited by examiner

*Primary Examiner* — D L Jones

(57) ABSTRACT

The invention relates to novel processes for the purification of radiolabelled tracers, using a solid-support bound scavenger group. The general concept being illustrated by the scheme:

7 Claims, No Drawings

PURIFICATION METHODS

This application is a filing under 35 U.S.C. 371 of international application number PCT/GB2005/001796, filed May 11, 2005, which claims priority to application number 0410448.5 filed May 11, 2004, in Great Britain the entire disclosure of which is hereby incorporated by reference.

The present invention relates to novel processes for the purification of radiolabelled tracers, in particular for purification of $^{18}$F- and $^{11}$C-labelled compounds which may be suitable for use as Positron Emission Tomography (PET) radiotracers or for radio-iodinated compounds which may be suitable for use in PET or SPECT imaging or in radiotherapy. Automated radiosynthesis apparatus, and disposable or removable cassettes therefor, adapted to perform the purification processes are also claimed.

Radiosynthesis of compounds of clinical interest often employs non-radioactive organic precursors in amounts which are in large excess relative to the amount of radiolabelling agent used. Excess precursors must be removed from the reaction mixture before the radiolabelled compound can be used clinically, this is conventionally done by a chromatographic procedure such as high performance liquid chromatography (HPLC). Given the limited half-life of most clinically useful radioisotopes, it is desirable to complete the radiosynthesis and purification as rapidly as possible. For example, $^{18}$F has a half-life of 110 minutes and $^{18}$F-labelled tracers for PET are therefore synthesised and purified within one hour of clinical use. Therefore, there exists a need for purification techniques which are rapid and efficient.

The present invention provides processes for separating radiolabelled compounds from their precursors rapidly and chemoselectively.

According to a general aspect of the invention, there is provided a process for purifying a radiolabelled product which comprises use of a solid-support bound scavenger group of formula (IV):

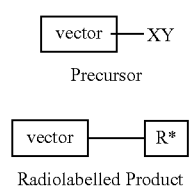
(IV)

wherein Z is a scavenger group and SP is a solid support.

In a further aspect of the invention, there is provided a process comprising the steps of:

(a) contacting a solution-phase mixture of a radiolabelled product of formula (III) and excess precursor of formula (I):

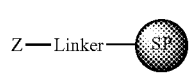

wherein XY is a functional group and R* is a radioisotope or radiolabelled portion; with a compound of formula (IV):

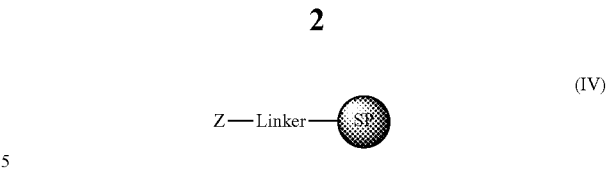
(IV)

wherein Z is a scavenger group;
such that the compounds of formulae (IV) and (I) may form a covalent bond to each other;

(b) separation of purified radiolabelled product of formula (III) in the solution phase.

Suitably, the radiolabelled product of formula (III) contains an $^{18}$F-label and is, for example 2-fluoro-2-deoxy-D-glucose ([$^{18}$F]-FDG), 6-fluoro-L-DOPA ([$^{18}$F]-FDOPA), 3'-deoxy-3'-fluorothymidine ([$^{18}$F]-FLT), [$^{18}$F]fluorotyrosine, 5-[$^{18}$F]fluorouracil, 5-[$^{18}$F]fluorocytosine, 2-(1,1-dicyanopropen-2-yl)-6-(2-fluoroethyl)-methylamino)-naphthalene ([$^{18}$F]-FDDNP), 2-, 5-, and 6-fluoro (2(S)-azetinylmethoxy)pyridines, N-succinimidyl-4-[$^{18}$F]fluorobenzoate ([$^{18}$F]-SFB), an $^{18}$F-labelled amino acid such as [$^{18}$F]-1-amino-3-fluorocyclobutane-1-carboxylic acid ([$^{18}$F]-FACBC), an [$^{18}$F]-labelled benzothiazole such as those described in international patent application WO 02/16333, a [$^{18}$F]fluorotropane such as 2β-carbomethoxy-3β-(4-[$^{18}$F]fluorophenyl)tropane ([$^{18}$F]CFT) or N-[$^{18}$F]fluoropropyl-2β-carbomethoxy-3β-(4-iodophenyl)nortropane ([$^{18}$F]FP-CIT), [$^{18}$F]FETNIM, [$^{18}$F]dopamine, an $^{18}$F-labelled peptide for example somatostatin analogues, such as octreotide, bombesin, vasoactive intestinal peptide, chemotactic peptide analogues, α-melanocyte stimulating hormone, neurotensin, Arg-Gly-Asp peptide and its analogues, human pro-insulin connecting peptide, endothelin, angiotensin and formyl-norleucyl-leucyl-phenylalanyl-norleucyl-tyrosyl-lysine, more suitably Arg-Gly-Asp peptide and its analogues, such as those described in international patent applications WO 01/77415 and WO 03/006491, or a protected derivative of any thereof.

Alternatively, the radiolabelled product of formula (III) contains a $^{11}$C-label and is, for example, [$^{11}$C]raclopride, [$^{11}$C-carboxyl]L-DOPA, [$^{11}$C-carboxyl]5-hydroxytryptophan, [$^{11}$C]-WAY-100635, [$^{11}$C]-deprenyl, [$^{11}$C]phenylephrine, [$^{11}$C]FLB457, [$^{11}$C]SCH23390, [$^{11}$C]SCH39166, [$^{11}$C]-NNC112, [$^{11}$C]NNC756, [$^{11}$C]MDL100907, [$^{11}$C]DSAB, [$^{11}$C]PK11195, [$^{11}$C]GR205171, [$^{11}$C]RTI-32, [$^{11}$C]CIT, [$^{11}$C]CFT, [$^{11}$C]flumazenil, [$^{11}$C]-diprenorphine, [$^{11}$C]-metomidate, [$^{11}$C]SCH442416, [$^{11}$C]carfentanil, or a $^{11}$C-labelled benzothiazole such as those described in international patent application WO 02/16333, or a protected derivative of any thereof.

Alternatively, the radiolabelled product of formula (III) contains a radioiodine label such as $^{131}$I, $^{123}$I, $^{124}$I, $^{122}$I or $^{125}$I, and is for example, 2-beta-carbomethoxy-3-beta-(4-iodophenyl)-8-(3-fluoropropyl)-nortropane or a protected derivative thereof.

The radiolabelled product of formula (III) comprises a vector portion being a molecular fragment having with an affinity for a given biological target (such as a modified drug pharmacaphore or peptide) and a radioisotope or radiolabelled portion represented by R*.

The precursor of formula (I) comprises the same vector portion as the radiolabelled product of formula (III) but bears a functional group —XY as described below.

Many radiosyntheses involve radioalkylation such as [$^{11}$C] alkylation, or radiohalogenation such as [$^{18}$F]fluorination or [$^{18}$F]fluoroalkylation, of precursors of formula (I). Treatment of the precursor with a radioisotope or radiolabelling agent of formula (II) gives rise to a mixture containing the desired radiolabelled product of formula (III) and excess unreacted precursor of formula (I). The precursor of formula (I) therefore contains a functional group —XY which is capable of reacting with the radioisotope or radiolabelling agent of formula (II) shown in scheme I. The functional group —XY is suitably a leaving group such as a sulphonate ester preferably the mesyl, tosyl, nosyl or is a trimethylammonium salt or is a functional group which can react site-specifically with a moiety on the radiolabelling agent of formula (II) to form a stable covalent bond and is preferably selected from the groups aldehydes, ketones, aminooxy, hydrazides, hydrazines, alpha-haloacetyl and thiol.

In the compound of formula (IV), the scavenger group Z is suitably an isocyanate, isothiocyanate, thiol, hydrazine, hydrazide, aminooxy, 1,3-dipole, aldehyde or ketone, such as those described in the more specific aspects of the invention below.

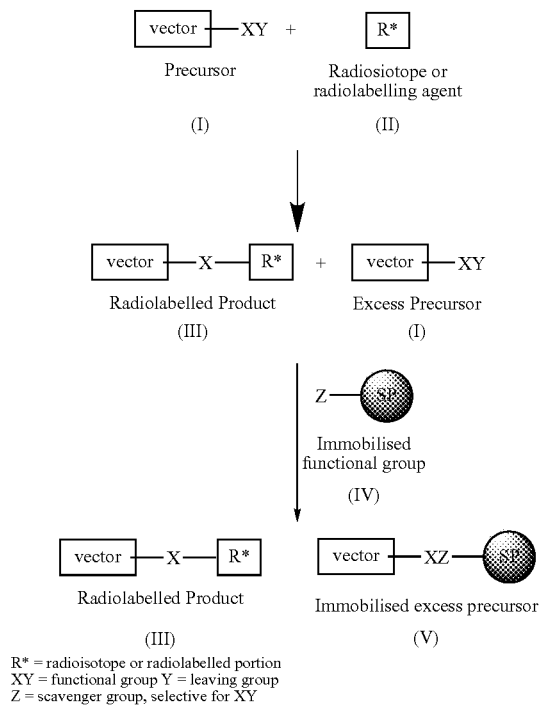

R* = radioisotope or radiolabelled portion
XY = functional group Y = leaving group
Z = scavenger group, selective for XY In the compounds of formulae (IV) and in the following more specific aspects of the invention, the solid support represented by SP, may be any suitable solid-phase support which is insoluble in any solvents to be used in the process but to which the Linker and/or scavenger group Z can be covalently bound. Examples of suitable Solid Support include polymers such as polystyrene (which may be block grafted, for example with polyethylene glycol), polyacrylamide, ring-opening metathesis polymerisation (ROMP) polymer, or polypropylene or glass or silicon coated with such a polymer. The solid support may also be sepharose based modified with suitable functional groups or derived from other known polymeric chromatographic media including ion exchange resins or C18 reverse-phase media. The solid support may be in the form of small discrete particles such as beads or pins, or as a coating on the inner surface of a cartridge or on a microfabricated vessel.

In the compounds of formulae (IV) and in the following more specific aspects of the invention, the "Linker" may be any suitable organic group which serves to space the scavenger group Z sufficiently from the solid support structure so as to maximise reactivity. Suitably, the Linker comprises zero to four aryl groups (suitably phenyl) and/or a $C_{1-6}$ alkyl or $C_{1-6}$ haloalkyl (suitably $C_{1-6}$ fluoroalkyl), and optionally one to four additional functional groups such as an amide or sulphonamide groups. In a preferred embodiment the linker is a polyethylene glycol containing moiety.

Compounds of formula (IV) may be prepared by methods known to the person skilled in the art (for a review of such methods, see Stabile-Harris and Ciampoli; Laboratory Automation in the Chemical Industries, 111-32 (2002)) or are available commercially, for example from Novabiochem (Merck Biosciences Ltd, Nottingham, UK) or from Argonaut (Mid Glamorgan, UK)

The purification may be performed by mixing the solid-support bound scavenger group of formula (IV) with a solution-phase mixture comprising a radiolabelled product of formula (III) in a container and then separating the resulting solid-phase by filtration. Alternatively, and particularly suitably when the solid-support bound scavenger group of formula (IV) is used within an automated synthesis apparatus, the solid-support bound scavenger group of formula (IV) may be contained in a vessel through which the solution-phase mixture comprising a radiolabelled product of formula (III) is passed. The solution-phase mixture comprising a radiolabelled product of formula (III) may be passed through the solid-support bound scavenger group of formula (IV) as a continuous flow, for example at a flow rate of from 0.1 ml/min to 100 ml/min, or in batches, so as to permit sufficient residence time on the solid-phase for the purification to occur. As would be understood by the person skilled in the art, the solid-support bound scavenger group of formula (IV) may be held in any suitable vessel such as a plastic or metal column, cartridge, or syringe barrel. The purification is conveniently performed at ambient temperature, but use of non-extreme elevated temperature (for example up to 120° C., but preferably up to around 80° C.) can increase efficiency of the extraction. If the temperature is too high, stability of the solid-support bound scavenger group of formula (IV) and/or radiolabelled product of formula (III) may be compromised.

In a further aspect of the invention, there is provided a process for purifying a radiolabelled product which comprises use of a solid-support bound isocyanate or isothiocyanate scavenger group. This process comprises the steps of:

(a) contacting a solution-phase mixture of a radiolabelled product of formula (IIIa) and excess precursor of formula (Ia):

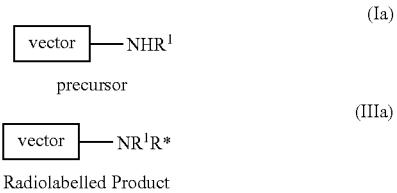

wherein $R^1$ is $C_{1-6}$ alkyl and R* is $[^{11}C]$-$C_{1-6}$alkyl, such as —$^{11}CH_3$ or $[^{18}F]$fluoro $C_{1-6}$ alkyl or $[^{18}F]$fluoro $C_{6-12}$ aryl;

with a compound of formula (IVa):

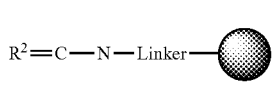

(IVa)

wherein R² is oxygen or sulphur
such that the compounds of formulae (IVa) and (Ia) may form a covalent bond to each other; and
(b) separation of purified radiolabelled product of formula (IIIa) in the solution phase.

The compounds of formula (IVa) and (Ia) react to form the corresponding urea or thiourea of formula (Va):

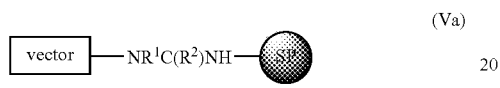

(Va)

wherein R¹ and R² are as defined for the compounds of formulae (Ia) and (IVa) respectively.

The purification process using a compound of formula (IVa) may be performed at a non-extreme temperature such as 10 to 120° C., suitably at ambient temperature to 80° C. and using an inert solvent such as xylene, N,N-dimethylformamide (DMF) or chloroform.

In this aspect of the invention, the compound of formula (IIIa) is suitably a $^{11}$C-labelled tertiary amine such as [$^{11}$C—CH$_3$]-2-Pyridin-4-yl-quinoline-8-carboxylic acid (2-dimethylamino-ethyl)-amide, [N-$^{11}$C-methyl]dimethylphenethylamine, or [$^{11}$C]DASB, and the precursor of formula (Ia) is the corresponding secondary amine such as 2-pyridin-4-yl-quinoline-8-carboxylic acid (2-methylamino-ethyl)-amide.

In a further aspect of the invention, there is provided a process for purifying a radiolabelled product which comprises use of a solid-support bound thiol scavenger group. This process comprises the steps of:
(a) contacting a solution-phase mixture of a radiolabelled product of formula (IIIb) and excess precursor of formula (Ib):

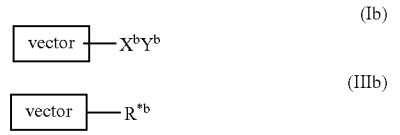

(Ib)

(IIIb)

wherein either
(i) the functional group —X$^b$Y$^b$ in the compound of formula (Ib) is —OSO$_2$R$^3$ wherein R$^3$ is C$_{1-15}$ alkyl or C$_{1-10}$ alkylaryl and R$^3$ is optionally substituted by halo (preferably fluoro), for example R$^3$ is methyl, para-toluene, trifluoromethyl, and R*$^b$ in the compound of formula (IIIb) is a radiohalogen such as radiofluoro (for example $^{18}$F) or radioiodo (such as $^{123}$I, $^{124}$I or $^{125}$I) or radiobromo (such as $^{76}$Br); or
(ii) the functional group —X$^b$Y$^b$ in the compound of formula (Ib) is —C(O)CH$_2$Cl and R*$^b$ in the compound of formula (IIIb) is —S-L$^b$-$^n$F wherein L$^b$ is a C$_{1-30}$ hydrocarbyl linker group optionally including 1 to 10 heteroatoms; and
$^n$F is a radioisotope of fluorine such as $^{18}$F;

with a compound of formula (IVb):

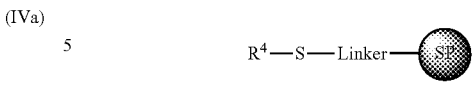

(IVb)

wherein R⁴ is hydrogen;
such that the compounds of formulae (IVb) and (Ib) may form a covalent bond to each other;
(b) separation of purified radiolabelled product of formula (IIIb) in the solution phase.

The compounds of formula (IVb) and (Ib) react to form the corresponding compound of formula (Vbi or Vbii):

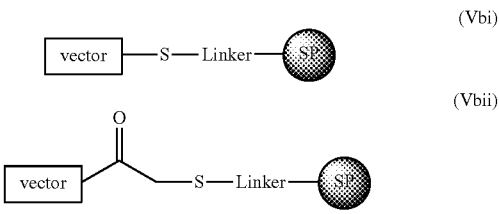

(Vbi)

(Vbii)

The purification process using a compound of formula (IVb) may be performed at a non-extreme temperature such as 10 to 120° C., suitably at ambient temperature to 80° C. and using an inert solvent such as xylene, N,N-dimethylformamide (DMF), DMSO, acetonitrile or chloroform. Preferably the solvent is an aqueous buffer or a mixture of acetonitrile and water or alcohol and water.

In a further aspect of the invention, there is provided a process for purifying a radiolabelled product which comprises use of a solid-support bound amino scavenger group. This process comprises the steps of:
(a) contacting a solution-phase mixture of a radiolabelled product of formula (IIIc) and excess precursor of formula (Ic):

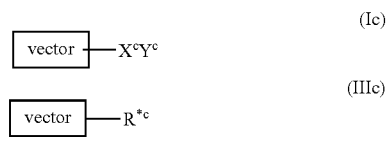

(Ic)

(IIIc)

wherein the functional group —X$^c$Y$^c$ in the compound of formula (Ic) is an aldehyde or ketone and R*$^c$ in the compound of formula (IIIc) is =N—W-Linker-F where W is C$_{1-15}$ alkyl or C$_{7-15}$ aryl, with a compound of formula (IVc):

(IVc)

wherein Z$^c$ is selected from —NH$_2$, hydrazine, hydrazide, aminooxy, phenylhydrazines, semicarbazide, or thiosemicarbazide;
such that the compounds of formulae (IVc) and (Ic) may form a covalent bond to each other; and
(b) separation of purified radiolabelled product of formula (IIIc) in the solution phase.

The compounds of formula (IVc) and (Ic) react to form the corresponding compound of formula (Vc):

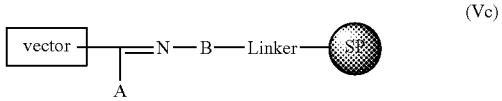

(Vc)

wherein A is hydrogen, $C_{1-6}$alkyl or aryl (such as phenyl) and B is —CO—NH—, —NH—, —O—, —NHCONH—, or —NHCSNH—.

In this aspect of the invention, compounds of the formula (IIc) have the formula $NH_2$—W-Linker-F where W is as described previously and F is preferably $^{18}F$ and the compound of formula (IIIc) is suitably a $^{18}F$-labelled compound such as a peptide or drug substance and the precursor of formula (Ic) is the corresponding aldehyde or ketone.

The purification process using a compound of formula (IVc) may be performed at a non-extreme temperature such as 10 to 120° C., suitably at ambient temperature to 80° C. and using an inert solvent such as xylene, N,N-dimethylformamide (DMF), DMSO, acetonitrile, or chloroform. Preferably the solvent is an aqueous buffer or a mixture of acetonitrile: water or alcohol and water.

In a further embodiment of this aspect of the invention, the functional group —$X^cY^c$ in the compound of formula (Ic) is —$OSO_2R^3$ wherein $R^3$ is $C_{1-15}$ alkyl or $C_{1-10}$ alkylaryl and $R^3$ is optionally substituted by halo (preferably fluoro), for example $R^3$ is methyl, para-toluene, trifluoromethyl; and the purification is effected using a compound of formula (IVci):

(IVci)

where W is selected from $C_{1-15}$ alkyl or $C_{7-15}$ aryl, —NH—, —NH—CO— or —O— and the linker is as described previously such that compounds of formula (Ic) and (IVci) form a covalent bond to each other.

The compounds of formula (IVci) and (Ic) react to form the corresponding compound of formula (Vci):

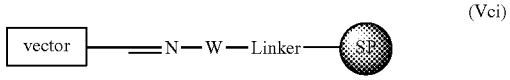

(Vci)

wherein W is as defined for the compound of formula (IVci).

In a further aspect of the invention, there is provided a process for purifying a radiolabelled product which comprises use of a solid-support bound aldehyde or ketone scavenger group. This process comprises the steps of:
(a) contacting a solution-phase mixture of a radiolabelled product of formula (IIId) and excess precursor of formula (Id):

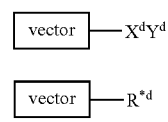

(Id)

(IIId)

wherein the functional group —$X^dY^d$ in the compound of formula (Id) is an amine, hydrazine, hydrazide, aminooxy, phenylhydrazine, or semicarbazide, thiosemicarbazide group and $R^{*d}$ in the compound of formula (IIId) is =CH-Linker-F where the linker comprises an alkyl, aryl or polyethylene glycol component;
with a compound of formula (IVd):

(IVd)

wherein $Z^d$ is an aldehyde or ketone moiety;
such that the compounds of formulae (IVd) and (Id) may form a covalent bond to each other; and
(b) separation of purified radiolabelled product of formula (IIId) in the solution phase.

The compounds of formula (Id) and (IVd) react to give compounds of formula (Vd):

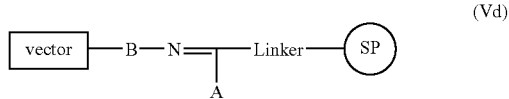

(Vd)

wherein A is hydrogen, $C_{1-6}$alkyl or aryl (such as phenyl) and B is —CO—NH—, —NH—, —O—, —NHCONH—, or —NHCSNH—.

The purification process using a compound of formula (IVd) may be performed at a non-extreme temperature such as 10 to 120° C., suitably at ambient temperature to 80° C. and using an inert solvent such as xylene, N,N-dimethylformamide (DMF), DMSO, acetonitrile or chloroform. Preferably the solvent is an aqueous buffer or a mixture of acetonitrile and water or alcohol and water.

In this aspect of the invention, the compound of formula (IIId) is suitably a $^{18}F$-labelled compound such as a peptide or drug and the precursor of formula (Id) is suitably a modified peptide or drug carrying an aminooxy ($NH_2$—O—), hydrazide or hydrazine moiety.

One particular compound of formula (IVd) which may be useful in this aspect of the invention, having a high loading of ketone scavenging group may be based on a ring-opening metathesis polymerisation (ROMP) polymer backbone. One of the main advantages of ROMP polymers is that in principle every monomer unit carries a functional group and should give much higher loading than some other polymers. ROMP is known for the production of functionalised polymers for organic synthesis (Barrett et al Chemical Reviews 2002 102 pp 3301-24). Suitable ROMP based polymers of formula (IVd) may be prepared by condensation of commercially available ketone alkene with furan followed by polymerisation, as shown in scheme 2:

scheme 2

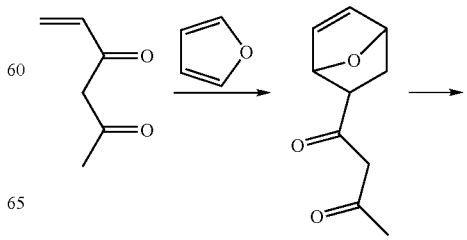

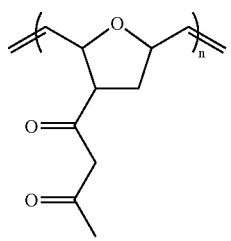

In a further aspect of the invention, there is provided a process for purifying a radiolabelled product which comprises use of a solid-support bound dipolar scavenger group. This process comprises the steps of (a) contacting a solution-phase mixture of a radiolabelled product of formula (IIIe) and a by-product (VIIe):

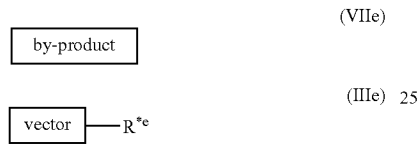

wherein the by-product (VIIe) contains an unwanted double bond, formed by an elimination side-reaction, and $R^{*e}$ in the compound of formula (IIIe) is radiohalo, particularly [$^{18}$F] fluoro;

with a compound of formula (IVe):

wherein $Z^e$ is a 1,3-dipole such as —N=N$^+$=N$^-$ or —C≡N$^+$—O$^-$
such that the compounds of formula (IVe) and (VIIe) may form a covalent bond to each other; and (b) separation of purified radiolabelled product of formula (IIIe) in the solution phase.

This aspect of the invention has particular relevance to synthesis of 3'-deoxy-3'-fluorothymidine ([$^{18}$F]-FLT) (IIIe) wherein a common by-product (VIIe) is formed by elimination of [$^{18}$F]HF from the sugar ring as shown in scheme 2:

Scheme 2

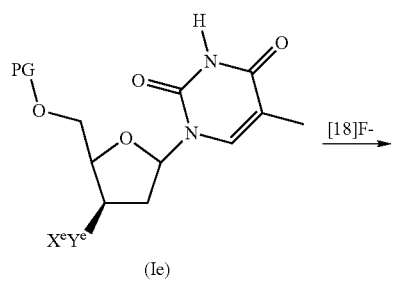

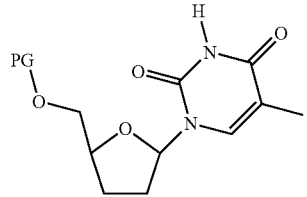

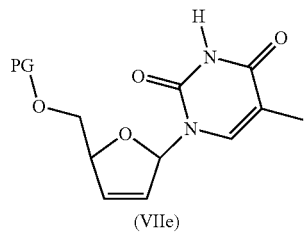

wherein each PG is hydrogen or a hydroxyl protecting group (suitably tert-butoxycarbonyl, benzyl, triphenylmethyl, or dimethoxytriphenylmethyl), and —$X^e Y^e$ is a suitable leaving group such as an alkyl- or aryl-sulphonate ester (for example trifluoromethane sulphonate, methane sulphonate, or toluene-para-sulphonate) or halo (such as iodo or bromo).

Purification using a compound of formula (IVe):

wherein $Z^e$ is a 1,3-dipole-A-E$^+$-G$^-$, such as —N=N$^+$=N$^-$ or —C≡N$^+$—O$^-$, gives a compound of formula (Ve) as shown in scheme 3:

Scheme 3

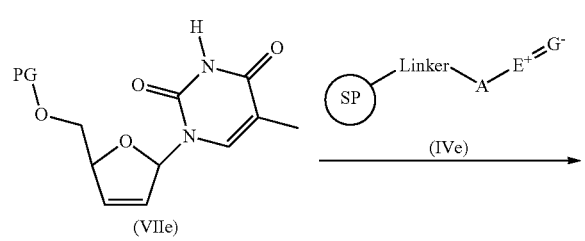

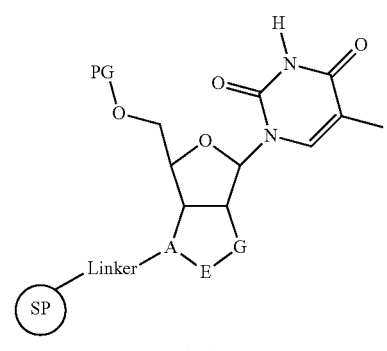

In a further aspect of the invention, a scavenger resin such as a compound of formula (IV) may also be used to react covalently with any unreacted radiolabelling agent of formula (II) as shown in scheme 4 to give compounds of formula (VI). This purification process may be used instead of, or in addition to, processes described herein for removal of excess precursor.

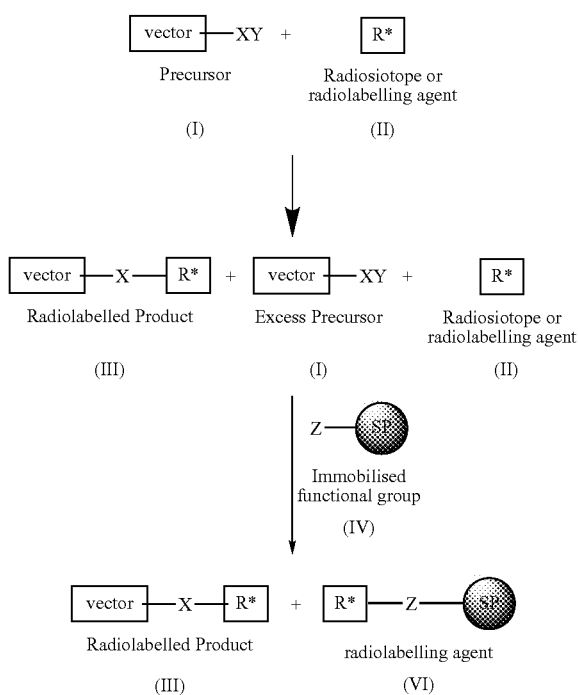

R* = radioisotope or radiolabelling agent
XY = functional group Y = leaving group
Z = scavenger group, selective for XY Thus, for example:

(i) A solid-support bound aldehyde or ketone scavenger group, such as a compound of formula (IVd) may facilitate removal of unreacted amino functionalised radiolabelling agent, such as a compound of formula (IIc) from a reaction mixture resulting in a compound of formula (VId):

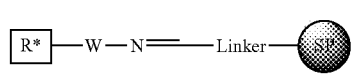
(VId)

(ii) A solid-support bound amino scavenger group, such as a compound of formula (IVc) may facilitate removal of unreacted radiolabelling agent having an aldehyde or ketone functionality resulting in a compound of formula (VIc).

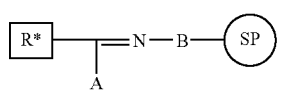
(VIc)

wherein A and B are as defined for the compound of formula (Vc).

(iii) A solid-support bound haloacetyl scavenger group, such as compound of formula (IVf)

(IVf)

may be used wherein $Z^f$ is Cl—$CH_2$—CO— or another haloacetyl containing moiety for removal of unreacted radiolabelling agent containing a thiol moiety of formula (II) from a reaction mixture results in compound of formula (VIf).

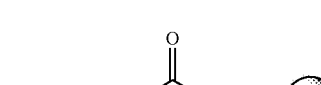
(VIf)

Radiotracers, such as [$^{18}$F]FDG are now often prepared on an automated radiosynthesis apparatus using nucleophilic radiofluorination chemistry with $^{18}$F$^-$, based on the reagent Kryptofix™ 2.2.2. There are several examples of such apparatus commercially available, including Tracerlab MX (Coincidence Technologies SA) and Tracerlab FX (Nuclear Interface GmbH). Such apparatus commonly comprises a cassette, often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges (typically $C_{18}$ or alumina) used in post-radiosynthetic clean up steps. The methods of the present invention may offer particular advantages in the field of automated radiosynthesis.

According to a further aspect of the invention, there is provided an automated radiosynthesis apparatus comprising a vessel, such as a cartridge, containing a solid-support bound scavenger group of formula (IV), (IVa), (IVb), (IVc), (IVd), (IVe), or (IVf).

The vessel, such as a cartridge, containing a solid-support bound scavenger group of formula (IV) may be housed in a disposable or removable cassette designed for use with the automated radiosynthesis apparatus. Therefore, the invention further provides a cassette for an automated radiosynthesis apparatus comprising a vessel, such as a cartridge, containing a solid-support bound scavenger group of formula (IV), (IVa), (IVb), (IVc), (IVd), (IVe), or (IVf).

The invention will now be illustrated by way of the following non-limiting examples.

EXAMPLES

Example 1

Use of an Isocyanate Resin for Purification of a $^{11}$C-Tracer

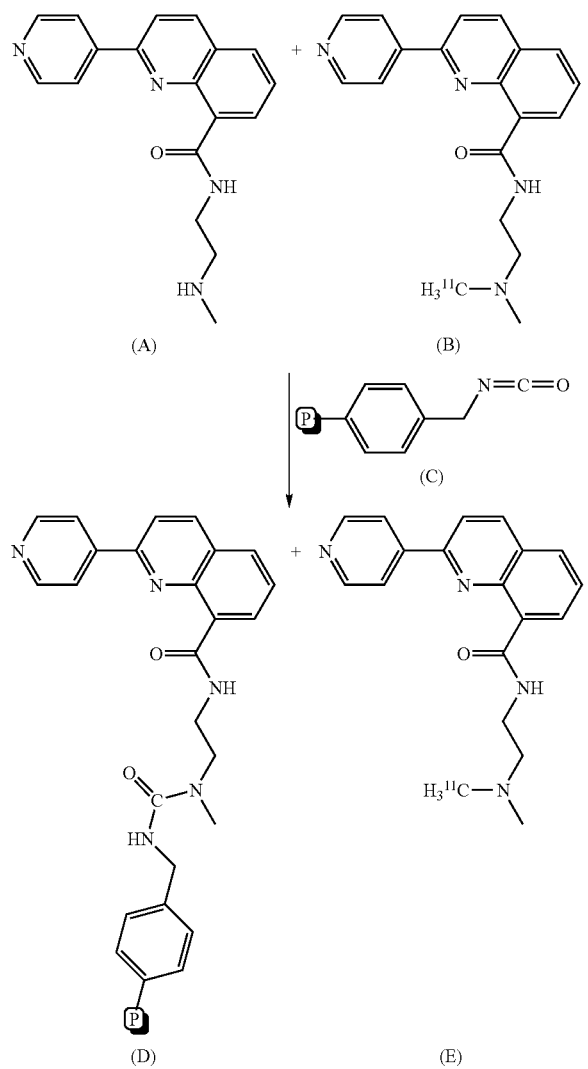

In both cases isocyanate resin was conditioned, using the same solvent as that from which precursor was to be extracted. Extraction efficiency was determined using HPLC. For studies using non-radioactive standard solutions, xylene was used as a control such that adjustments could be made for non-specific extraction and solvent loss.

Example 1(a)

In Situ Resin Conditioning and Solid Phase Extraction (SPE) at Elevated Temperatures A cartridge (internal volume 0.067 ml) made of 3.2 mm (⅛") o.d. steel tubing and circular frits was charged with 25 mg of dry isocyanate functionalised polystyrene resin (Novabiochem). Solvent ca 5 ml (dichloromethane (DCM), N,N-dimethylformamide (DMF) or dimethylsulphoxide (DMSO)) was then passed through the cartridge and excess solvent removed with compressed air. For studies at elevated temperature a two-piece heater block, thermocouple and band heater were fitted around the cartridge and the entire assembly left ca 10 min to thermally equilibrate. 500 µl of solution containing precursor 2-Pyridin-4-yl-quinoline-8-carboxylic acid (2-methylamino-ethyl)-amide (A) 0.5 mg and Xylene 1.3 mg were then passed through the cartridge using a syringe drive. Using this method, SPE efficiency was dependent on the solvent used, with extraction efficiency decreasing in the order DCM (67%), DMF (36%), and DMSO (<5%) at room temperature.

Example 1(b)

SPE with External Resin Conditioning

For external conditioning 300 mg of isocyanate resin (Novabiochem) was suspended in excess solvent ca 9 ml for ca 5 min. The conditioned resin slurry was then loaded onto a 0.8 ml volume cartridge made of 6 mm (⅜") steel tubing. Excess solvent was removed with compressed air. Precursor solutions 300 µl or reaction mixture from automated preps 300 µl were passed through the cartridge using a syringe drive. A 1 ml syringe gave flow rates of 0.4 ml min$^{-1}$, equating to a contact time ca 2 min.

Example 1(c)

SPE Purification of [$^{11}$C—CH$_3$] 2-Pyridin-4-yl-quinoline-8-carboxylic acid (2-dimethylamino-ethyl)-amide Reaction Mixtures Following [$^{11}$C]radiolabelling, 300 µl of the resulting reaction mixture (A+B) was drawn up from the reaction vial and dispensed (using a syringe drive) at a flow of 444 µl min$^{-1}$ through one of the conditioned isocyanate resin cartridges detailed in Examples 1(a) and 1(b). The cartridge was then flushed with 500 µl of chloroform and the combined solutions analysed by HPLC. The cartridge was then flushed with a further 3 aliquots of 500 µl chloroform. Cumulative product recovery after SPE using the external conditioning method of Example 1(b) was 90% with precursor levels at circa 4% of the levels found in the non-purified reaction mixture.

What is claimed is:

1. A process for purifying a radiolabelled product comprising the steps of:
   (i) reacting a precursor with a radioisotope or radiolabeling agent to form a solution-phase radiosynthesis reaction mixture comprising a radiolabelled product and excess precursor;
   (ii) contacting said solution-phase radiosynthesis reaction mixture with a solid-support bound scavenger group of formula (IV):

(IV)

wherein:
Z is a scavenger group selected from the group consisting of: isocyanate, isothiocyanate, thiol, hydrazine, hydrazide, aminooxy, 1,3-dipole, aldehyde, ketone, —NH$_2$, H$_2$N—C$_{1-15}$alkyl, H$_2$N—C$_{7-15}$aryl, H$_2$N—

NH—, H$_2$N—NH—C(=O), H$_2$N—O—, phenylhydrazines, semicarbazide, and thiosemicarbazide; and SP is a solid support;

wherein said excess precursor forms a covalent bond with said solid support bound scavenger group of formula (IV); and (iii) separating said radiolabelled product in the solution-phase; and wherein: said excess precursor is of formula (I) and said radiolabelled product is of formula (III):

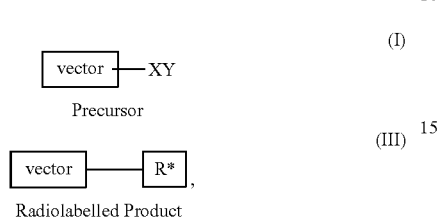

(I)

Precursor (III)

Radiolabelled Product wherein XY of Formula (I) is either a leaving group capable of reacting with said radioisotope or said radiolabeling agent of Formula (II):

R*   (II)

and is a mesyl sulphonate ester, tosyl sulphonate ester, nosyl sulphonate ester, or a trimethylammonium salt; or a functional group which can react site-specifically with a moiety on said radiolabeling agent of Formula (II) and is an aldehyde, ketone, aminooxy, hydrazide, hydrazine, alpha-haloacetyl, or thiol.

2. The process according to claim 1 wherein said excess precursor is of formula (Ia) and said radiolabelled product is of formula (IIIa):

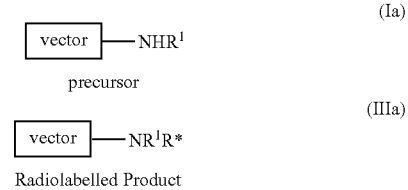

(Ia)

precursor (IIIa)

Radiolabelled Product wherein R$^1$ is C$_{1-6}$ alkyl and R* is [$^{11}$C]—C$_{1-6}$alkyl, [$^{18}$F]fluoro C$_{1-6}$ alkyl or [$^{18}$F]fluoro C$_{6-12}$ aryl;

and Z of the compound of formula (IV) is isocyanate or isothiocyanate.

3. The process according to claim 1 wherein said excess precursor is of formula (Ib) and said radiolabelled product is of formula (IIIb):

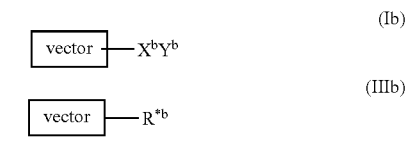

(Ib)

(IIIb)

wherein either (i) the functional group —X$^b$Y$^b$ in the compound of formula (Ib) is —OSO$_2$R$^3$ wherein R$^3$ is C$_{1-15}$ alkyl or C$_{1-10}$ alkylaryl and R$^3$ is optionally substituted by halo and R*$^b$ in the compound of formula (IIIb) is a radiohalogen; or (ii) the functional group —X$^b$Y$^b$ in the compound of formula (Ib) is —C(O)CH$_2$Cl and R*$^b$ in the compound of formula (IIIb) is —S-L$^b$-$^n$F wherein L$^b$ is a C$_{1-30}$ hydrocarbyl linker group optionally including 1 to 10 heteroatoms; and $^n$F is a radioisotope of fluorine; and Z of the compound of formula (IV) is thiol.

4. The process according to claim 1 wherein said excess precursor is of formula (Ic) and said radiolabelled product is of formula (IIIc):

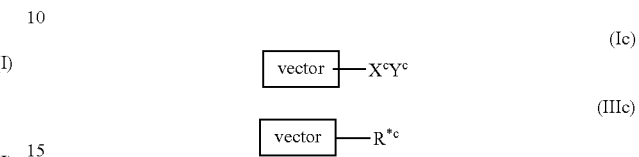

(Ic)

(IIIc)

wherein the functional group —X$^c$Y$^c$ in the compound of formula (Ic) is an aldehyde or ketone and R*$^c$ in the compound of formula (IIIc) is =N—W-Linker-F where W is C$_{1-15}$ alkyl or C$_{7-15}$ aryl; and Z of the compound of formula (IV) is —NH$_2$, hydrazine, hydrazide, aminooxy, phenylhydrazines, semicarbazide, or thiosemicarbazide.

5. The process according to claim 1 wherein said excess precursor is of formula (Ic) and said radiolabelled product is of formula (IIIc):

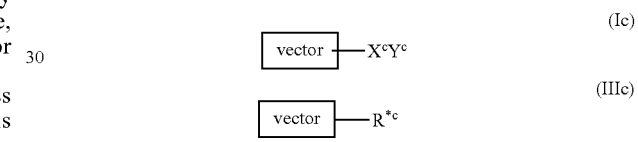

(Ic)

(IIIc)

wherein the functional group —X$^c$Y$^c$ in the compound of formula (Ic) is —OSO$_2$R$^3$ wherein R$^3$ is C$_{1-15}$ alkyl or C$_{1-10}$ alkylaryl and R$^3$ is optionally substituted by halo and R*$^c$ in the compound of formula (IIIc) is =N—W-Linker-F where W is C$_{1-15}$ alkyl or C$_{7-15}$ aryl; and Z of the compound of formula (IV) is H$_2$N—C$_{1-15}$alkyl, H$_2$N—C$_{7-15}$aryl, H$_2$N—NH—, H$_2$N—NH—C(=O), or H$_2$N—O—.

6. The process according to claim 1 wherein said excess precursor is of formula (Id) and said radiolabelled product is of formula (IIId):

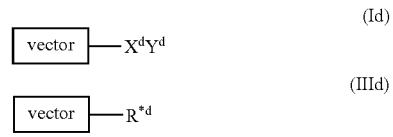

(Id)

(IIId)

wherein the functional group —X$^d$Y$^d$ in the compound of formula (Id) is an amine, hydrazine, hydrazide, aminooxy, phenylhydrazine, semicarbazide, or thiosemicarbazide group and R*$^d$ in the compound of formula (IIId) is =CH-Linker-[18F]F where the linker comprises an alkyl, aryl or polyethylene glycol component; and Z of the compound of formula (IV) is an aldehyde or ketone.

7. The process according to claim 6 wherein Z is a ketone based on a ring-opening metathesis polymerisation (ROMP) polymer backbone.

* * * * *